United States Patent

Mano et al.

Patent Number: 5,925,677
Date of Patent: Jul. 20, 1999

[54] LACRIMATION ACCELERATING AGENT

[75] Inventors: Tomiya Mano; Shunji Sogo, both of Osaka, Japan

[73] Assignee: Mitsubishi Chemical Corporation, Tokyo, Japan

[21] Appl. No.: 08/876,425

[22] Filed: Jun. 16, 1997

Related U.S. Application Data

[30] Foreign Application Priority Data

Jun. 17, 1996 [JP] Japan ................................. 8-155176

[51] Int. Cl.$^6$ ..................... A61K 31/235; A61K 31/24; A61K 31/135
[52] U.S. Cl. ........................................... 514/543; 514/651
[58] Field of Search ..................... 514/543, 651

[56] References Cited

U.S. PATENT DOCUMENTS

| | | | |
|---|---|---|---|
| 4,485,258 | 11/1984 | Kikumoto et al. | 562/471 |
| 4,599,419 | 7/1986 | Kikumoto et al. | 544/301 |
| 5,244,902 | 9/1993 | Sharpe et al. | 514/278 |

FOREIGN PATENT DOCUMENTS

| | | |
|---|---|---|
| 0 398 326 | 11/1990 | European Pat. Off. . |
| 0 522 226 | 1/1993 | European Pat. Off. . |
| 0 695 545 | 2/1996 | European Pat. Off. . |
| WO92/04015 | 3/1992 | WIPO . |

OTHER PUBLICATIONS

Katzung, *Basic & Clinical Pharmacology*, Sixth Edition, p. 143, 1995.

Zifa et al., *Pharmacological Reviews*, vol. 44, No. 3 (1962), pp. 401 and 424–432.

Ali et al., Database Medline Accession No. 89297619, XP002041344 (Abstract) *Rev. Elev. Med. Vet. Pays Trop.*, vol. 42, No. 1, 1989, pp. 13–17.

Adeghate et al., *Biogenic. Amines*, vol. 10, No. 2, pp. 487–498 (1994).

*Primary Examiner*—Alan L. Rotman
*Attorney, Agent, or Firm*—Wenderoth, Lind & Ponack, L.L.P.

[57] ABSTRACT

A lacrimation accelerating agent containing a ligand of serotonin receptor as an active ingredient. Also provided is a method for preventive and/or therapeutic treatment of a disease caused by a deficiency of lacrimal fluid such as dry eye, which comprises the step of administering to a mammal an effective amount of a ligand of a serotonin receptor such as sarpogrelate hydrochloride.

8 Claims, No Drawings

LACRIMATION ACCELERATING AGENT

BACKGROUND OF THE INVENTION

1. Field of the Invention

The present invention relates to a lacrimation accelerating agent comprising a ligand of a serotonin receptor as an active ingredient.

2. Related Art

A great number of people are bothered with diseases caused by deficiency of lacrimal fluid such as those diagnosed as dry eye, xerophthalmia, keratitis sicca or the like. One of the main causes of these diseases is considered as autoimmune disorder called Sjögren's syndrome, and possibilities of treatment from this point of view have been studied (New Ophthalmology, 11(8), pp.1187–1195, 1994). For xerophthalmia due to Sjögren's syndrome, it was reported that anetholtrithion promoted lacrimation (Diagnosis and New Drug, 26(11), pp.105–127, 1989). It was also reported that instillation of vitamin A was effective for dry eye (New Ophthalmology, 10(10), 1685–1686, 1993).

Although various efforts have been made to develop medicaments for the diseases caused by the deficiency of lacrimal fluid, e.g., dry eye, any satisfactory medicament has not yet been found.

SUMMARY OF THE INVENTION

An object of the present invention is to provide a novel medicament for accelerating secretion of lacrimal fluid.

Another object of the present invention is to provide a method for preventive and/or therapeutic treatment of a disease caused by a deficiency of lacrimal fluid.

The inventors of the present invention first revealed that a ligand of a serotonin receptor has lacrimation accelerating activity, and on the basis of the findings, they achieved the present invention.

Various research has been conducted concerning serotonin receptors, and ligands of serotonin receptors have been revealed to have various kinds of physiological functions (Pharmacological Reviews, 44(3), 401). However, it has not been reported that a ligand of a serotonin receptor has lacrimation accelerating activity.

The present invention thus provide a lacrimation accelerating agent comprising a ligand of a serotonin receptor as an active ingredient.

According to another aspect of the present invention, there is provided a method for preventive and/or therapeutic treatment of a disease caused by a deficiency of lacrimal fluid, which comprises a step of administering to a mammal an effective amount of a ligand of a serotonin receptor.

According to further embodiment of the present invention, there is also provided a pharmaceutical composition for preventive and/or therapeutic treatment of a disease caused by a deficiency of lacrimal fluid, which comprises a ligand of a serotonin receptor as an active ingredient together with a pharmaceutically acceptable additive.

According to still further embodiment of the present invention, there is provided a use of a ligand of a serotonin receptor for the manufacture of said pharmaceutical composition for preventive and/or therapeutic treatment of a disease caused by a deficiency of lacrimal fluid which comprises a ligand of serotonin receptor as an active ingredient.

DETAILED DESCRIPTION OF THE INVENTION

Best Mode for Carrying out the Invention

Serotonin receptors are classified into various types, and numbers of ligands are known for each of the types. Any one of these ligands can be used for the present invention. Among them, ligands of receptor (2) are preferably used. Examples of such ligands include agonists such as 1-(2,5-dimethoxy-4-bromophenyl)-2-aminopropane (DOB), 1-(2,5-dimethoxy-4-iodophenyl)-2-aminopropane (DOI), and N-(3-trifluoro-methylphenyl)piperazine (YFMPP), and antagonists, such as chloropromazine, ritanserin, ketanserin, cinanserine, butaclamol, and metergoline (Pharmacological Reviews, 44(3), 401). Among these compounds, particularly preferred compounds include aminoalkoxybibenzyl compounds represented by the following formula (I), as being serotonin antagonists, pharmaceutically acceptable salts thereof, and solvates thereof:

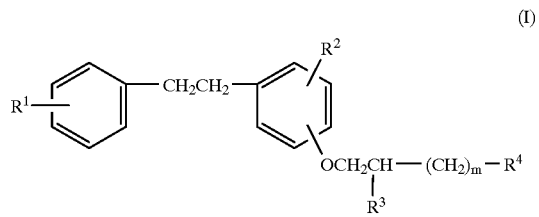

(I)

wherein $R^1$ represents a hydrogen atom, a halogen atom, a $C_1$–$C_5$ alkoxy group, or a $C_2$–$C_6$ dialkylamino group; $R^2$ represents a hydrogen atom, a halogen atom, or a $C_1$–$C_5$ alkoxy group; $R^3$ represents a hydrogen atom, hydroxyl group, —O—$(CH_2)_n$—COOH wherein the symbol "n" represents an integer of from 1 to 5, or —O—CO—$(CH_2)_l$—COOH wherein the symbol "l" represents an integer of from 1 to 3; $R^4$ represents —N($R^5$)($R^6$) wherein $R^5$ and $R^6$ each independently represent a hydrogen atom or a $C_1$–$C_8$ alkyl group, or $R^4$ represents

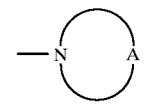

wherein A represents a $C_3$–$C_5$ alkylene group which may be substituted with a carboxyl group; and the symbol "m" represents an integer of from 0 to 5. The term "salt" herein used has the broadest meaning so as to include an ester.

It is known that the compounds of the formula (I) as serotonin antagonists are effective for improvement of various sorts of microcirculatory disturbance owing to thrombogenesis and vasoconstriction in diseases such as cerebral circulatory disturbance, ischemic heart disease, peripheral circulation disturbance and the like (the Japanese Patent Unexamined Publication (KOKAI) No. (Hei) 2-304022/1990). It is also known that they are effective for the treatment of glaucoma and reducing ocular tension (the Japanese Patent Unexamined Publication (KOKAI) No. (Hei) 8-20531/1996). However, it is totally unexpected that the aforementioned compounds have lacrimation accelerating activity.

The compounds of the formula (I) will be more specifically explained. In the formula, $R^1$ represents a hydrogen atom; a halogen atom such as a chlorine atom or a fluorine atom; a $C_1$–$C_5$ alkoxy group such as methoxy group, ethoxy group, or butoxy group; or a $C_2$–$C_6$ dialkylamino group such as dimethylamino group, diethylamino group, and methylethylamino group. $R^2$ represents a hydrogen atom; a halogen atom such as chlorine atom or a fluorine atoms; and a $C_1$–$C_5$ alkoxy group such as methoxy group, ethoxy group, or butoxy group. $R^3$ represents a hydrogen atom; hydroxyl group; —O—$(CH_2)_n$—COOH (the symbol "n" represents an integer of from 1 to 5) such as —O—$(CH_2)_2$—COOH or —O—$(CH_2)_3$—COOH; or —O—CO—$(CH_2)_l$—COOH (the symbol "l" represents an integer of from 1 to 3) such as —O—CO—$(CH_2)_2$—COOH or —O—CO—$(CH_2)_3$—COOH. $R^4$ represents a non-substituted amino group or an amino groups having one or two $C_1$–$C_8$ alkyl groups such as methylamino group, ethylamino group, butylamino group, hexylamino group, heptylamino group, dimethylamino group, diethylamino group, or methylethylamino group; or $R^4$ represents a 4- to 6-membered polymethyleneamino group whose ring may be substituted with a carboxyl group, such as trimethyleneamino group, pentamethyleneamino group, or 3-carboxypentamethyleneamino group.

Among the compounds according to Formula (I), some of those preferably used for the invention are shown in Table 1.

present invention. Examples of acids used for the formation of such salts include hydrochloric acid, hydrobromic acid, sulfuric acid, phosphoric acid, nitric acid, acetic acid, succinic acid, adipic acid, propionic acid, tartaric acid, maleic acid, oxalic acid, citric acid, benzoic acid, toluensulfonic acid, methanesulfonic acid and the like. Solvates of the compounds according to the above formula (1) or salts thereof, e.g., hydrates, may also be used for the present invention. Among them, an example of particularly preferred substances includes (±)-1-[O-[2-(m-methoxyphenyl)ethyl]phenoxy]-3-(dimethylamino)-2-propylhydrogen succinate hydrochloride represented by the following formula (IV) (this compound will be referred to as "sarpogrelate hydrochloride" hereinafter in the specification).

TABLE 1

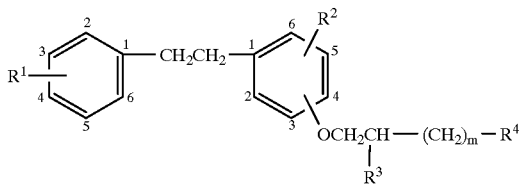

| Compound No. | $R^1$ | $R^2$ | Position of Aminoalkoxy Group | $R^3$ | m | $R^4$ |
|---|---|---|---|---|---|---|
| 1 | H | H | 2- | H | 0 | $N(CH_3)_2$ |
| 2 | H | H | 2- | H | 1 | $N(CH_3)_2$ |
| 3 | H | H | 2- | H | 2 | $N(CH_3)_2$ |
| 4 | H | H | 2- | H | 3 | $N(CH_3)_2$ |
| 5 | H | H | 2- | H | 4 | $N(CH_3)_2$ |
| 6 | H | H | 2- | H | 2 | $NHCH_3$ |
| 7 | H | H | 2- | H | 2 | $NH_2$ |
| 8 | H | H | 2- | H | 2 | 1-piperidino |
| 9 | H | H | 2- | H | 2 | 4-carboxy-1-piperidino |
| 10 | H | H | 3- | H | 2 | $N(CH_3)_2$ |
| 11 | H | H | 4- | H | 2 | $N(CH_3)_2$ |
| 12 | 3-$OCH_3$ | H | 2- | H | 2 | $N(CH_3)_2$ |
| 13 | 4-$N(CH_3)_2$ | H | 2- | H | 1 | $N(CH_3)_2$ |
| 14 | 3-$OCH_3$ | H | 2- | $OCO(CH_2)_2COOH$ | 1 | $N(CH_3)_2$ |
| 15 | 3-$OCH_3$ | H | 2- | OH | 1 | $N(CH_3)_2$ |
| 16 | 3-$OCH_3$ | H | 2- | $O(CH_2)_2COOH$ | 1 | $N(CH_3)_2$ |
| 17 | 3-F | H | 2- | $OCO(CH_2)_2COOH$ | 1 | $N(CH_3)_2$ |
| 18 | H | H | 2- | OH | 1 | $N(CH_3)_2$ |
| 19 | 3-Cl | H | 2- | H | 2 | $N(CH_3)_2$ |
| 20 | H | 5-Cl | 2- | H | 2 | $N(CH_3)_2$ |
| 21 | H | 3-$OCH_3$ | 2- | H | 2 | $N(CH_3)_2$ |

As for these compounds, the aminoalkoxy group represented by —$OCH_2$—$C(R^3)H$—$(CH_2)_m$—$R^4$ may preferably bind to the 2-position of the phenyl group. $R^1$ is preferably a hydrogen atom, a $C_1$–$C_5$ alkoxy group, or a $C_2$–$C_6$ dialkylamino group; $R^2$ is preferably a hydrogen atom; $R^4$ is preferably an amino group having at least one $C_1$–$C_8$ alkyl group or a 4- to 6-membered polymethyleneamino group having trimethylene group or pentamethylene group, and m is preferably an integer of from 0 to 2. Particularly preferred compounds include Compound No. 15 wherein $R^1$ is methoxy group; $R^2$ is a hydrogen atom; $R^3$ is hydroxyl group, and $R^4$ is dimethylamino group (this compound will be referred to as "M-1" hereinafter in the specification) and the succinic acid ester thereof, i.e., Compound No. 14.

Pharmaceutically acceptable salts of the compounds according to the above formula (1) may also be used for the

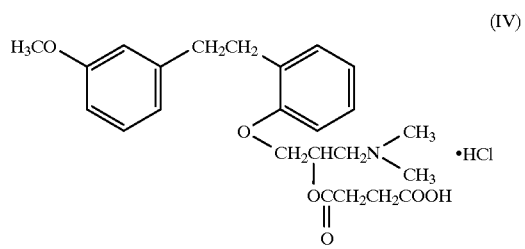

(IV)

The aminoalkoxybibenzyl compounds of the formula (I) used for the present invention are known compounds as previously mentioned, and can be easily prepared according to the method described in the Japanese Patent Unexamined Publication (KOKAI) No. (Sho) 58-32847/1983 or methods with some modifications thereto.

The lacrimation accelerating agent of the present invention promotes the secretion of lacrimal fluid without ophthalmic irritation, and therefore, the agent is useful for preventive and/or therapeutic treatments of various diseases or symptoms such as dry eye, keratitis sicca, or xerophthalmia that require an acceleration of lacrimation and protection of cornea.

The lacrimation accelerating agent of the present invention can be administered as oral preparations, injections, eye drops, or ointment. In the case of oral preparations, the preparations may be in any one of conventional dosage forms such as tablets, capsules, powders, liquid preparations, or elixirs. For example, in the case of capsules, ordinary gelatin-type capsules may be used. Tablets and powders may contain various kinds of pharmaceutical additives commonly used for pharmaceutical preparations. These capsules, tablets, and powders may usually contain from 5 to 95% by weight, preferably from 25 to 90% by weight of the active ingredient.

For liquid preparations, various kinds of naturally-derived or synthetic liquids such as water, mineral oil, soybean oil, peanut oil, sesame oil, propylene glycol, or polyethylene glycol may be used. In the case of the liquid preparations for oral administration, the active ingredients may be dissolved or dispersed in the aforementioned liquids so as to be from 0.5 to 20% by weight. They may also be added with commonly used additives such as perfumes, saccharides, or surfactants.

Injections may be prepared so as to contain from 0.5 to 20% by weight, preferably from 1 to 10% by weight of the active ingredient in physiological saline.

In the case of eye drops, the active ingredient may dissolve in water at from 0.001 to 1% by weight, and then the solution may optionally be added with various kinds of ordinary additives such as buffering agents, isotonic agents, antiseptics, or thickeners.

Examples of the buffering agents include phosphate buffer, borate buffer, citrate buffer, tartrate buffer, acetate buffer, and amino acids.

As the isotonic agent, for example, saccharides such as sorbitol, glucose, or mannitol; polyhydric alcohols such as glycerin or propylene glycol; or salts such as sodium chloride may be used.

As the antiseptic, for example, quaternary ammonium salts such as benzalkonium chloride or benzethonium chloride; p-hydroxybenzoic acid esters such as methyl p-hydroxybenzoate or ethyl p-hydroxybenzoate; benzyl alcohol; phenethyl alcohol; sorbic acid or salts thereof; thimerosal; or chlorobutanol can be used.

As the thickener, for example, hydroxyethylcellulose, hydroxypropylcellulose, methylcellulose, hydroxypropylmethylcellulose, carboxymethylcellulose, or salts thereof may be used.

Ointments may be prepared by uniformly mixing from 0.1 to 1% by weight of the active ingredient with a suitable base such as vaseline, followed by optionally mixing preservatives, stabilizers, or other suitable additives.

Dose of the lacrimation accelerating agent of the present invention may vary depending on age and body weight of patients, symptoms, severity of diseases and the like, which should be ultimately decided by physicians. Generally, the dose as being the amount of an ingredient may be from 0.5 to 50 mg/kg body weight per day, usually from 1 to 30 mg/kg body weight per day, and such dose may be administered for one or more days. More specifically, in the case of oral preparation, unit dosage forms may be prepared so as to contain 50 mg or 100 mg of the active ingredient, and usually administered once to three times a day. In the case of injection, 10 to 30 mg of the active ingredient may be usually administered once to four times a day. Eye drops may be administered once to four times a day.

EXAMPLES

The present invention will be explained more specifically by referring to the examples set out below. However, the scope of the present invention is not limited to these examples.

Accelerating activities of sarpogrelate hydrochloride, M-1, and ketanserin on the secretion of lacrimal fluid were examined by using male Japanese white rabbits having a body weight of about 2 to 2.5 kg. For the experiments, sarpogrelate hydrochloride and M-1 were dissolved in physiological saline at 0.1% by weight (pH 6.5 to 7.0 and pH 5.5 to 5.8, respectively), and ketanserin was dissolved in physiological saline at 0.4% by weight (pH 4.7). As sarpogrelate hydrochloride and M-1, those prepared according to the methods described in the Japanese Patent Unexamined Publication (KOKAI) No. (Sho) 58-32847/1983 were used. As ketanserin, a commercial product was used that had been purchased from Funakoshi.

Example 1

To the eyes of five of the rabbits, 0.4% oxybuprocaine hydrochloride (Santen Pharmaceutical Co. Ltd.) was instilled twice with an interval of 3 minutes in an amount of 30 $\mu$l for each of the instillations. After three minutes, moisture in conjunctival sacs was absorbed with an imbibition paper, and then sarpogrelate hydrochloride solution was instilled to one of the eyes of an animal and physiological saline to the other eye in the respective volume of 50 $\mu$l. After three minutes from the instillation, moisture in conjunctival sacs was again absorbed with an imbibition paper, and after 10 minutes, lacrimal fluid was collected by inserting a filter paper strip (3×30 mm) between the lower eyelid and the conjunctival bulbi and weighed. The amount of lacrimal fluid in the eyes instilled with sarpogrelate hydrochloride solution was 6.0±0.4 mg, whereas the amount in the eyes instilled with physiological saline was 2.1±0.6 mg, which was found to be significantly smaller. Any conspicuous behavior indicating the existence of ophthalmic irritation due to the administered drugs such as closing eye or nictation was not observed after the instillation.

Example 2

The experiments were carried out precisely according to Example 1 except that 10 rabbits were subjected to the experiments and filter paper strips having a size of 5×30 mm were used. The amount of lacrimal fluid in the eyes instilled with sarpogrelate hydrochloride solution was 7.4±0.8 mg, whereas the amount of lacrimal fluid in the eyes instilled with physiological saline was 5.1±0.6 mg, which was found to be significantly smaller. Any conspicuous behavior indicating the existence of ophthalmic irritation due to the administered drugs such as closing eye and nictation was not observed after the instillation.

Example 3

To the eyes of ten of the rabbits, 0.4% oxybuprocaine hydrochloride (Santen Pharmaceutical Co. Ltd.) was instilled twice with an interval of 3 minutes in an amount of 30 μl for each of the instillations. After three minutes, moisture in conjunctival sacs was absorbed with an imbibition paper, and then M-1 solution or physiological saline was instilled to one of the eyes of an animal in the respective volume of 50 μl. After 10 and 20 minutes, lacrimal fluid was collected by inserting a filter paper strip (5×30 mm) between the lower eyelid and the conjunctival bulbi and weighed. As a result, the amount of lacrimal fluid after 10 minutes from the instillation was 6.7±0.9 mg for the group instilled with M-1 solution, whereas 4.4±0.5 mg for the group instilled with physiological saline. The amount of lacrimal fluid after 20 minutes was 7.3±0.7 mg for the group instilled with M-1 solution, whereas 5.1±0.4 mg for the group instilled with physiological saline. The results obtained by the control group were found to be significantly smaller than those obtained by the group instilled with M-1 solution. Any conspicuous behavior indicating the existence of ophthalmic irritation due to the administered drugs such as closing eye and nictation was not observed after the instillation.

Example 4

By using five rabbits, 50 μl of the ketanserin solution was instilled to one of the eyes of the rabbits. As a result, remarkable lacrimation was observed. Any conspicuous behavior indicating the existence of ophthalmic irritation due to the administered drugs such as closing eye and nictation was not observed after the instillation.

What is claimed is (for U.S.):

1. A method for the therapeutic treatment of a disease caused by a deficiency of lacrimal fluid selected from the group consisting of dry eye, xerophthalmia and keratitis sicca, comprising the step of administering to a mammal in need of such treatment an effective amount of a ligand of a serotonin receptor, wherein said ligand is an antagonist of a serotonin receptor (2) and is an aminoalkoxydibenzyl compound, a pharmaceutically acceptable salt thereof, or a solvate thereof represented by the following formula (I):

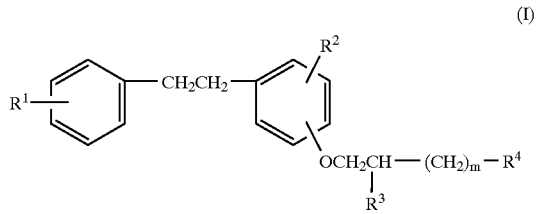

(I)

wherein $R^1$ represents a hydrogen atom, a halogen atom, a $C_1$–$C_5$ alkoxy group, or a $C_2$–$C_6$ dialkylamino group; $R^2$ represents a hydrogen atom, a halogen atom, or a $C_1$–$C_5$ alkoxy group; $R^3$ represents a hydrogen atom, hydroxyl group, —O—$(CH_2)_n$—COOH wherein the symbol "n" represents an integer of from 1 to 5, or —O—CO—$(CH_2)_l$—COOR wherein the symbol "l" represents an integer of from 1 to 3; $R^4$ represents —N($R^5$)($R^6$) wherein $R^5$ and $R^6$ each independently represent a hydrogen atom or a $C_1$—$C_8$ alkyl group, or $R^4$ represents

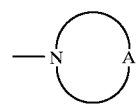

wherein A represents a $C_3$–$C_5$ alkylene group which is optionally substituted with a carboxyl group; and the symbol "m" represents an integer of from 0 to 5.

2. A method for accelerating secretion of lacrinal fluid in a mammal comprising the step of administering to a mammal an effective amount of a ligand of a serotonin receptor, wherein said ligand is an antagonist of a serotonin receptor (2) and is an aminoalkoxydibenzyl compound, a pharmaceutically acceptable salt thereof, or a solvate thereof represented by the following formula (I):

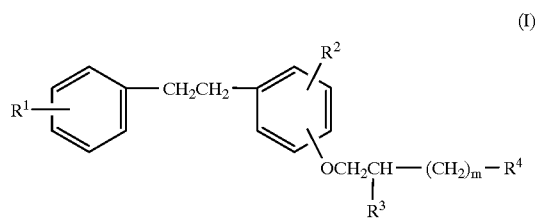

(I)

wherein $R^1$ represents a hydrogen atom, a halogen atom, a $C_1$–$C_5$ alkoxy group, or a $C_2$–$C_6$ dialkylamino group; $R^2$ represents a hydrogen atom, a halogen atom, or a $C_1$–$C_5$ alkoxy group; $R^3$ represents a hydrogen atom, hydroxyl group, —O—$(CH_2)_n$—COOH wherein the symbol "n" represents an integer of from 1 to 5, or —O—CO—$(CH_2)_l$—COOH wherein the symbol "l" represents an integer of from 1 to 3; $R^4$ represents —N($R^5$)($R^6$) wherein $R^5$ and $R^6$ each independently represent a hydrogen atom or a $C_1$–$C_8$ alkyl group, or $R^4$ represents

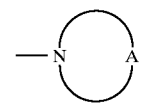

wherein A represents a $C_3$–$C_5$ alkylene group which is optionally substituted with a carboxyl group; and the symbol "m" represents an integer of from 0 to 5.

3. The method according to claim 2, wherein said antagonist of a serotonin receptor (2) is a substance selected from the group consisting of a compound represented by the following formula (II), a salt thereof, and a solvate thereof

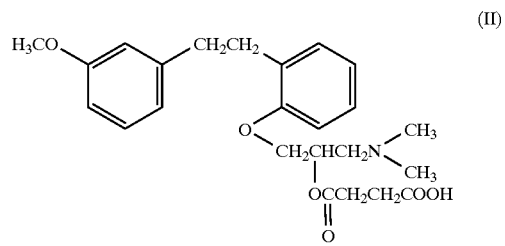

(II)

4. The method according to claim 2, wherein said antagonist of a serotonin receptor (2) is a substance selected from the group consisting of a compound represented by the following formula (III), a salt thereof, and a solvate thereof

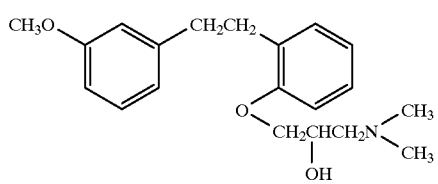
(III)

5. The method according to claim 2, wherein said step of administration is carried out by instillation.

6. The method according to claim 1, wherein said antagonist of a serotonin receptor (2) is a substance selected from the group consisting of a compound represented by the following formula (II), a salt thereof, and a solvate thereof.

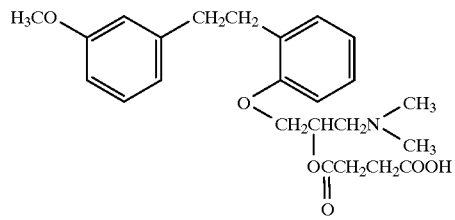
(II)

7. The method according to claim 1, wherein said antagonist of a serotonin receptor (2) is a substance selected from the group consisting of a compound represented by the following formula (III), a salt thereof, and a solvate thereof.

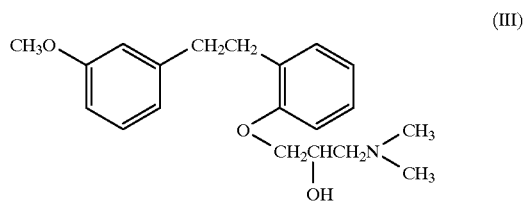
(III)

8. The method according to claim 1, wherein said step of administration is carried out by instillation.

* * * * *